United States Patent [19]
Conkling et al.

[11] Patent Number: 6,008,436
[45] Date of Patent: Dec. 28, 1999

[54] NEMATODE-RESISTANT TRANSGENIC PLANTS

[75] Inventors: Mark A. Conkling, Fuquay-Varina; Charles H. Opperman, Raleigh; Gregoria N. Acedo, Durham; Wen Song, Raleigh, all of N.C.

[73] Assignee: North Carolina State University, Raleigh, N.C.

[21] Appl. No.: 08/654,025

[22] Filed: May 23, 1996

Related U.S. Application Data

[63] Continuation of application No. 08/332,658, Nov. 1, 1994, abandoned, which is a continuation of application No. 08/007,998, Jan. 21, 1993, abandoned.

[51] Int. Cl.$^6$ ............................ C12N 15/00; C12N 15/29; C12N 15/82; A01H 5/00
[52] U.S. Cl. .......................... 800/301; 800/295; 800/317; 800/314; 536/23.6; 536/24.1; 536/24.5; 435/320.1; 435/419; 435/468; 435/469; 435/470
[58] Field of Search .............................. 435/172.1, 172.3, 435/240.4, 320.1, 419; 536/23.6, 24.1, 24.5; 800/205, DIG. 40, DIG. 42, DIG. 43, DIG. 23, DIG. 27, DIG. 26, DIG. 54

[56] References Cited

U.S. PATENT DOCUMENTS

| | | |
|---|---|---|
| 4,940,840 | 7/1990 | Suslow et al. . |
| 4,948,734 | 8/1990 | Edwards et al. ...................... 435/252.5 |
| 5,015,580 | 5/1991 | Christou et al. ...................... 435/172.3 |
| 5,034,323 | 7/1991 | Jorgensen et al. .................... 435/172.3 |
| 5,093,120 | 3/1992 | Edwards et al. ........................... 424/93 |

FOREIGN PATENT DOCUMENTS

| | | | |
|---|---|---|---|
| 0 307 841 | 9/1987 | European Pat. Off. ......... C12N 15/00 |
| 0 375 091 | 12/1988 | European Pat. Off. .......... C12N 1/21 |
| 0 298 918 | 1/1989 | European Pat. Off. ......... C12N 15/00 |
| 0 425 004 | 5/1991 | European Pat. Off. ......... C12N 15/40 |
| 0427529A1 | 5/1991 | European Pat. Off. ....... A01N 65/00 |
| 0 479 180 | 4/1992 | European Pat. Off. ......... C12N 15/11 |
| 42 04103 | 8/1993 | Germany .......................... C12N 9/00 |
| WO 89/00194 | of 1989 | WIPO .............................. C12N 1/06 |
| WO 90/07936 | 7/1990 | WIPO ............................. A61K 39/12 |
| WO 91/13994 | 9/1991 | WIPO ............................. C12N 15/83 |
| WO91/13992 | 9/1991 | WIPO . |
| WO92/04453 | 3/1992 | WIPO . |
| WO 92/21757 | 12/1992 | WIPO ............................. C12N 15/29 |
| WO92/21757 | 12/1992 | WIPO . |
| WO 93/06710 | 4/1993 | WIPO .............................. A01H 1/00 |
| WO 93/10251 | 5/1993 | WIPO ............................. C12N 15/82 |
| WO 93/18170 | 9/1993 | WIPO ............................. C12N 15/82 |
| WO 93/19188 | 9/1993 | WIPO ............................. C12N 15/82 |

OTHER PUBLICATIONS

Evans et al. The effects of ribozymes on gene expression in plants. Biochemical Society Transactions (1992) 20, p. 344.
R. Hartley; Barnase and Barstar Expression of Its Cloned Inhibitor Permits Expression of a Cloned Ribonuclease; *J. Mol. Biol.* 202 pp. 913–915 (1988).
C.H. Opperman et al; Reproduction of Three Root–Knot Nematodes on Winter Small Grain Crops; *Plant Disease* 72 pp. 869–871 (1988).
C.J. Paddon et al; Translation and Processing of *Bacillus amyloliquefaciens* Extracellular RNase; *Journal of Bacteriology* 171 pp. 1185–1187 (1989).
C.J. Paddon et al; Cloning, sequencing and transcription of an inactivated copy of *Bacillus amyloliquefaciens* extracellular ribonuclease (barnase); *Gene* 40 pp. 231–239 (1986).
Y. T. Yamamoto et al; A Tobacco Root–Specific Gene: Characterization and Regulation of Its Expression; *J. Cell Biochem.* 13D p. 313 (1989).
T. Maniatis et al; Regulation of Inducible and Tissue–Specific Gene Expression; *Science* 236; pp. 1237–1244 (1987).
W.J. Gordon–Kamm et al; Transformation of Maize Cells and Regeneration of Fertile Transgenic Plants; *The Plant Cell* 2, pp. 603–618 (1990).
K. Takahashi et al; Requirement of stereospecific alignments for initiation from the simian virus 40 early promoter; *Nature* 319, pp. 121–126 (1986).
A. Niebel et al; Molecular Analysis of Nematode–Induced Giant Cells in Potato Roots; *J. Cell Biochem;* 13 Part D; p. 323 (1989).
M. S. Chapekar et al; The Synergistic Cytocidal Effect Produced by Immune Interferon and Tumor Necrosis Factor in HT–29 Cells is Associated with Inhibition of rRNA Processing and (2', 5') Oligo (A) Activation of RNase L; *Biochim. Biophys. Res. Comm* 151 pp. 1180–1187 (1988).
P. Shaw et al; The Two Promoters of the Mouse α–Amylase Gene Amy–1$^a$ Are Differentially Activated during Parotid Gland Differentiation; *Cell* 40 pp. 907–912 (1985).
C. Mariani et al; Induction of male sterility in plants by a chimaeric ribonucelase gene; *Nature* 347 pp. 737–741 (1990).
C.H. Opperman, et al; Root–Knot Nematode–Directed Expression of a Plant Root–Specific Gene, *Science* 263,pp. 221–223 (1994).
Sarah Jane Gurr, et al.; *Mol Gen Genet*, 226, 361–366 (1991).

(List continued on next page.)

*Primary Examiner*—Douglas W. Robinson
*Assistant Examiner*—Thomas Haas
*Attorney, Agent, or Firm*—Myers Bigel Sibley & Sajovec

[57] ABSTRACT

Nematode-resistant transgenic plants are disclosed. The plants comprise plant cells containing a DNA construct comprising a transcription cassette, which construct comprises, in the 5' to 3' direction, a promoter operable in the plant cells, and a DNA comprising at least a portion of a DNA sequence encoding a nematode-inducible transmembrane pore protein in either the sense or antisense orientation. Intermediates for producing the same along with methods of making and using the same are also disclosed. In an alternate embodiment of the invention, the sense or antisense DNA is replaced with a DNA encoding an enzymatic RNA molecule directed against the mRNA transcript of a DNA sequence encoding a nematode-inducible transmembrane pore protein.

53 Claims, 1 Drawing Sheet

OTHER PUBLICATIONS

Dick Inze et al., *J. Cell Biochem.,* Suppl. O, 13, Part D, 323 (1989).

Mark A. Conkling et al., *Plant Physiol 93,* 1203–1211 (1990).

*Business Week 99,* Science & Technology "Starve A. Worm, Save a Plant" (1991).

M. G. K. Jones, *Ann. appl. Biol. 97,* 353–372 (1981).

Yamamoto et al. 1990. Nucleic Acids Research. 18(24):7449.

Tomes et al. 1990. Plant Molecular Biology 14:261–268.

Yamamoto et al. 1991. The Plant Cell. 3:371–382.

Delauney et al. 1988. Proc. Natl. Acad. USA. 85:4300–4304.

Evans et al. 1992. Biochemical Society Transactions. 20:344S.

Haseloff et al. 1988. Nature. 334(18):585–591.

NEMATODE-RESISTANT TRANSGENIC PLANTS

This is a continuation of application Ser. No. 08/332,658, now abandoned filed on Nov. 1, 1994 which is a file wrapper continuation of Ser. No. 08/007,998 filed on Jan. 21, 1993 now abandoned.

This invention was made with government support under Grant No. DMB-88-11077 awarded by the National Science Foundation. The government has certain rights in the invention.

FIELD OF THE INVENTION

This invention relates to methods of controlling plant-parasitic nematodes by application of recombinant DNA technology and the production of transgenic plants.

BACKGROUND OF THE INVENTION

World-wide, plant-parasitic nematodes are among the most devastating pathogens of life sustaining crops. In 1984, nematodes accounted for more than fifty billion dollar s (US) in economic losses. The United States' portion of this figure alone is almost six billion dollars. Genetic resistance to certain nematode species is available in some cultivars, but these are restricted in number, and the availability of cultivars with both desirable agronomic features and resistance is limited. In addition, traditional methods for plant breeding require 5–10 years to produce a viable cultivar, while the need for new nematode control tools is immediate and critical.

The major means of nematode control has been the application of chemical nematicides. During 1982, in the United States alone over 100 million pounds of nematicide were applied to crops. Chemical nematicides are generally highly toxic compounds known to cause substantial environmental impact. In the past several years, issues such as ground water contamination, mammalian and avian toxicity, and residues in food have caused much tighter restrictions on the use of chemical nematicides. Unfortunately, in many situations there is no alternative available for growers who rely upon nematicides to protect their crop from root-knot and cyst nematodes. Accordingly, there is a continuing need for new ways to combat nematodes in plants.

SUMMARY OF THE INVENTION

A first aspect of the present invention is a DNA construct comprising a transcription cassette. The construct comprises, in the 5' to 3' direction, (a) a promoter operable in a plant cell, (b) a DNA comprising at least 15 nucleotides of a DNA sequence encoding a nematode-inducible transmembrane pore protein in either the opposite orientation for expression (i.e., an antisense DNA) or the proper orientation for expression (i.e., a sense DNA), and (c) optionally, but preferably, a termination signal. The promoter may be one which is constitutively active in plant cells, selectively active in plant root tissue cells, or a nematode-responsive element such as the nematode-responsive element of the Tobacco RB7 (TobRB7) promoter. Such constructs may be carried by a plant transformation vector such as an *Agrobacterium tumefaciens* vector, which are in turn used to produce recombinant plants.

A second aspect of the present invention is, accordingly, a nematode-resistant transgenic plant. The plant comprises cells containing a DNA construct comprising a transcription cassette as described above.

In particular embodiments of the invention, DNA encoding a nematode-inducible transmembrane pore protein may be selected from the group consisting of: (a) isolated DNA having the sequence given herein as SEQ ID NO:1 (which DNA encodes the nematode-inducible transmembrane pore protein given herein as SEQ ID NO:2) or SEQ ID NO:6 (which is a genomic DNA encoding the nematode-inducible transmembrane pore protein given herein as SEQ ID NO:7, which is the same as SEQ ID NO:2); (b) isolated DNA which hybridizes to isolated DNA of (a) above and which encodes a nematode inducible transmembrane pore protein (which isolated DNA is preferably at least 50% homologous with an isolated DNA of (a) above; and which pore protein is preferably at least 60% homologous with a pore protein of (a) above); and (a) isolated DNA differing from the isolated DNAs of (a) and (b) above in nucleotide sequence due to the degeneracy of the genetic code, and which encode a nematode-inducible transmembrane pore protein. A specific example of such a DNA, in antisense configuration for carrying out the present invention, is given herein as SEQ ID NO:3.

Additionally, in particular embodiments of the invention, DNA encoding a nematode-responsive element may be selected from the group consisting of: (i) isolated DNA having the sequence given herein as SEQ ID NO:5; and (ii) isolated DNA which hybridizes to isolated DNA of (i) above and which encodes a nematode responsive element (which is preferably at least 60% homologous to isolated DNA of (i) above; and which are preferably at least 10 or 15 nucleotides in length) (this definition is intended to include fragments of (i) above which retain activity as nematode-responsive elements).

The foregoing and other objects and aspects of this invention are explained in detail in the drawings herein and the specification set forth below.

DETAILED DESCRIPTION OF THE INVENTION

Figure 1:
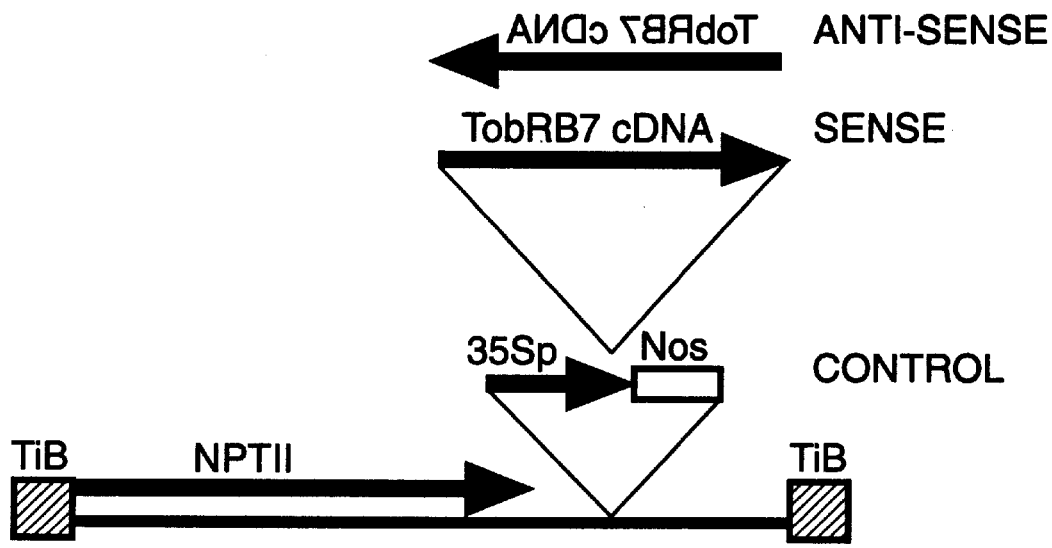
FIG. 1 illustrates a pair of DNA constructs comprising transcription cassettes, one in which the TobRB7 cDNA in sense configuration under the transcriptional control of a CaMV 35S promoter, and the other with a TobRB7 cDNA in antisense configuration under the transcriptional control of a CaMV 35S promoter. A nos 3' termination sequence and a neomycin phosphotransferase II (NPT-II) selectable marker for imparting kanamycin resistance is provided in both cases. The border regions of the Ti plasmid into which the cassette is inserted are indicated as "TiB".

The present invention is employed to combat nematodes, particularly the root knot nematodes (Meloidogyne spp.) and the cyst nematodes (Globodera spp. and Heterodera spp.). These nematodes have similar life cycles. Root-knot nematodes are sedentary endoparasites with an extremely intimate and complex relationship to the host plant. The infective second stage juvenile (J2) is free in the soil. Upon location of a host root, the J2 penetrates the root intercellularly in the region just posterior to the root cap and migrates to the developing vascular cylinder. The nematode then orients itself parallel to the cylinder and injects glandular secretions into the plant cells surrounding its head, resulting in the initiation of nematode feeding cells. These 5–7 cells undergo rapid nuclear divisions, increase tremendously in size, and become filled with pores and cell wall invaginations. The feeding site cells, or "giant cells", function as super transfer cells to provide nourishment to the developing nematode. During this time, the nematode loses the ability to move and swells from the normal eel shaped J2 to a large, pear shaped adult female. As the nematode feeds on the giant cells, parthenogenic reproduction results in the the disposition of 300–1000 eggs. This entire process occurs over the span of 20–30 days, and root-knot nematodes may complete as many as 7 generations during a cropping season. The life cycle of the cyst nematode is essentially the same, except that its feeding site is referred to as a "syncytia", and it undergoes sexual reproduction.

Nematode-inducible transmembrane pore proteins are pore proteins the expression of which is increased in cells upon infection of a plant containing the cells by a plant-parasitic nematode at a position adjacent those cells. Increased expression of such pore proteins is required by the nematode in establishing a feeding site capable of passing nutrients from the plant to the nematode. In general, and as explained in greater detail below, DNA encoding nematode-inducible transmembrane pore proteins include DNA which is 50% homologous or more with DNA having the sequence given herein as SEQ ID NO:1 or SEQ ID NO:6. With respect to the protein, DNA encoding nematode-inducible transmembrane pore proteins encode a protein which, in amino acid content, is about 60% homologous or more, or preferably about 70% homologous or more, with the protein having the amino acid sequence given herein as SEQ ID NO:2. Determinations of homology are made with the two sequences (nucleic acid or amino acid) aligned for maximum matching. Gaps in either of the two sequences being matched are allowed in maximizing matching. Gaps lengths of 10 or less are preferred, gap lengths of 5 or less are more preferred, and gap lengths of 2 or less still more preferred.

Differential hybridization procedures are available which allow for the isolation of cDNA clones whose mRNA levels are as low as about 0.05% of poly(A$^+$)RNA. See M. Conkling et al., *Plant Physiol.* 93, 1203–1211 (1990). In brief, cDNA libraries are screened using single-stranded cDNA probes of reverse transcribed mRNA from plant tissue (i.e., roots and leaves). For differential screening, a nitrocellulose or nylon membrane is soaked in 5×SSC, placed in a 96 well suction manifold, 150 μL of stationary overnight culture transferred from a master plate to each well, and vacuum applied until all liquid has passed through the filter. 150 μL of denaturing solution (0.5M NaOH, 1.5 M NaCl) is placed in each well using a multiple pipetter and allowed to sit about 3 minutes. Suction is applied as above and the filter removed and neutralized in 0.5 M Tris-HCl (pH 8.0), 1.5 M NaCl. It is then baked 2 hours in vacuo and incubated with the relevant probes. By using nylon membrane filters and keeping master plates stored at −70° C. in 7% DMSO, filters may be screened multiple times with multiple probes and appropriate clones recovered after several years of storage.

For example, to isolate genes whose expression is induced or enhanced by nematode infection, a cDNA library of mRNA isolated from nematode infected tobacco roots is constructed. The roots are staged such that mRNA is isolated at the time of giant cell initiation. The library is then screened by the procedures given above using single stranded cDNA probes of mRNA isolated from nematode-infected and control roots. Those cDNA clones exhibiting differential expression are then used as probes on tobacco genomic Southern blots (to confirm the cDNA corresponds to tobacco and not nematode transcripts) and Northern blots of root RNA from infected and control tissue (to confirm differential expression). Those clones exhibiting differential expression are then used as probes to screen an existing tobacco genomic library. Essentially the same procedure is carried out with plants other than tobacco and nematodes (or other pathogens) other than root-knot nematodes. The procedure is useful for identifying promoters induced by cyst nematodes, in which case the roots are staged such that mRNA is isolated at the time of syncytia initiation. For example, a potato-cyst nematode (*Globodera* spp.) inducible promoter is isolated from potato plants (*Solanum tuberosum*) in accordance with the foregoing procedures.

We have probed a wide variety of dicotyledonous and monocotyledonous plants at low stringency with TobRB7 probes and have found that most (if not all) plants contain a TobRB7 analog. We have already identified by low stringency hybridization such a root-specific cDNA analog from *Arabidopsis thaliana* (AtRB7) (Yamamoto, Cheng, and Conkling 1990 *Nucl. Acids Res.* 18: 7449).

Nematode-inducible transmembrane pore proteins employed in carrying out the present invention include proteins homologous to, and having essentially the same biological properties as, the nematode-inducible pore protein Tobacco RB7 disclosed herein as SEQ ID NO:2 (the same as SEQ ID NO:7). This definition is intended to encompass natural allelic variations in the pore protein. Cloned genes employed in carrying out the present invention may code for a nematode-inducible pore protein of any species of origin, including tobacco, soybean, potato, peanuts, pineapple, cotton, and vegetable crops, but preferably encode a nematode-inducible transmembrane pore protein of dicot origin. Thus, DNA sequences which hybridize to DNA of SEQ ID NO:1 or SEQ ID NO:6 and code on expression for a nematode-inducible transmembrane pore protein may also be employed in carrying out the present invention. Conditions which will permit other DNA sequences which code on expression for a pore protein to hybridize to a DNA having the sequence given as SEQ ID NO:1 or SEQ ID NO:6 can be determined in a routine manner. For example, hybridization of such sequences may be carried out under conditions of reduced stringency or even stringent conditions (e.g., conditions represented by a wash stringency of 0.3 M NaCl, 0.03 M sodium citrate, 0.1% SDS at 60° C. or even 70° C. to DNA having the sequence given as SEQ ID NO:1 or SEQ ID NO:6 herein in a standard in situ hybridization assay. See J. Sambrook et al., Molecular Cloning, A Laboratory Manual (2d Ed. 1989) (Cold Spring Harbor Laboratory)). In general, such sequences will be at least 75% homologous, 80% homologous, 85% homologous, 90% homologous, or even 95% homologous or more with the sequence given herein as SEQ ID NO:1 or SEQ ID NO:6 (in the case of SEQ ID NO:6, which is a genomic sequence, such homology is with respect to the exons alone, though the homology may be considered with respect to both introns and exons). Determinations of homology are made with the two sequences aligned for maximum matching. Gaps in either of the two sequences being matched are allowed in maximizing matching. Gap lengths of 10 or less are preferred, gap lengths of 5 or less are more preferred, and gap lengths of 2 or less still more preferred.

Antisense DNAs in the present invention are used to produce the corresponding antisense RNAs. An antisense RNA is an RNA which is produced with the nucleotide bases in the reverse or opposite order for expression. Such antisense RNAs are well known. See, e.g., U.S. Pat. No. 4,801,540 to Calgene Inc. In general, the antisense RNA will be at least 15 nucleotides in length, and more typically at least 50 nucleotides in length. The antisense RNA may include an intron-exon junction (i.e., one, two, or three nucleotides on either or both sides of the intron-exon junction). Antisense RNAs which include an intron-exon junction are constructed with reference to a genomic DNA sequence.

Sense DNAs employed in carrying out the present invention are of a length sufficient to, when expressed in a plant cell, supress the native expression of a nematode-inducible transmembrane pore protein as described herein in that plant cell. Such sense DNAs may be essentially an entire genomic or complementary DNA encoding the nematode-inducible transmembrane pore protein or a fragment thereof, with such fragments typically being at least 15 nucleotides in length.

In an alternate embodiment of the present invention, the sense or antisense DNA in the construct is replaced with a DNA encoding an enzymatic RNA molecule (i.e., a "ribozyme"), which enzymatic RNA molecule is directed against (i.e., cleaves) the mRNA transcript of a DNA encoding a nematode-inducible transmembrane pore protein as described hereinabove. DNA encoding enzymatic RNA molecules may be produced in accordance with known techniques. See, e.g., T. Cech et al., U.S. Pat. No. 4,987,071 (the disclosure of which is to be incorporated herein by reference). Production of such an enzymatic RNA molecule and disruption of pore protein production combats the infection of plants by nematodes in essentially the same manner as production of an antisense RNA molecule: that is, by disrupting translation of mRNA in the cell which produces the pore protein.

Promoters employed in carrying out the present invention may be constitutively active promoters. Numerous constitutively active promoters which are operable in plants are available. A prefered example is the Cauliflower Mosaic Virus (CaMV) 35S promoter. In the alternative, the promoter may be a root-specific promoter or a nematode-responsive element, as explained in greater detail below.

Promoters which are selectively active in plant root tissue cells employed in carrying out the present invention include DNAs homologous to, and having essentially the same biological properties as, the Tobacco RB7 root-specific gene promoter disclosed herein as SEQ ID NO:4. This definition is intended to encompass natural allelic variations therein. Such elements may be of any species of origin, including tobacco, soybean, potato, peanuts, pineapple, cotton, and vegetable crops, but preferably are of dicot origin. Thus, DNA sequences which hybridize to DNA of SEQ ID NO:4 and contain a root-specific gene promoter may also be employed in carrying out the present invention. Conditions which will permit other DNA sequences which code for a such an element to hybridize to a DNA having the sequence given as SEQ ID NO:4 can be determined in a routine manner. For example, hybridization of such sequences may be carried out under conditions as given above in connection with nematode-inducible transmembrane pore proteins. Such sequences will generally be at least 75% homologous, 80% homologous, 85% homologous, 90% homologous, or even 95% homologous or more with the sequence given herein as SEQ ID NO:4. Gaps may be introduced to maximize homology when determining homology, as discussed above. In addition, homology may be determined with respect to a 10 to 15 or even 25 or 50 base segment of a DNA having the sequence of SEQ ID NO:5 and capable of directing nematode-responsive transcription of a downstream DNA sequence (i.e., a structural gene or an antisense DNA) in a plant cell. By "base segment" is meant a continuous portion thereof which is of the indicated number of nucleotides in length.

Nematode-responsive elements employed in carrying out the present invention include DNAs homologous to, and having essentially the same biological properties as, the Tobacco RB7 nematode-responsive element disclosed herein as SEQ ID NO:5. This definition is intended to encompass natural allelic variations therein. Such elements may again be of any species of origin, including tobacco, soybean, potato, peanuts, pineapple, cotton, and vegetable crops, but preferably are of dicot origin. Thus, DNA sequences which hybridize to DNA of SEQ ID NO:5 and contain a nematode-responsive element may also be employed in carrying out the present invention. Conditions which will permit other DNA sequences which code for a such an element to hybridize to a DNA having the sequence given as SEQ ID NO:5 can again be determined in a routine manner. For example, hybridization of such sequences may be carried out under conditions as given above in connection with nematode-inducible transmembrane pore proteins. Such sequences will generally be at least 75% homologous, 80% homologous, 85% homologous, 90% homologous, or even 95% homologous or more with the sequence given herein as SEQ ID NO:5. Gaps may be introduced to maximize homology when determining homology, as discussed above. In addition, homology may be determined with respect to a 10 to 15 or even 25 or 50 base segment of a DNA having the sequence of SEQ ID NO:5 and capable of directing nematode-responsive transcription of a downstream DNA sequence (i.e., a structural gene or an antisense DNA) in a plant cell.

DNA constructs, or "transcription cassettes," of the present invention include, 5' to 3' in the direction of transcription, a promoter as discussed above, a DNA operatively associated with the promoter, and, optionally, a termination sequence including stop signal for RNA polymerase and a polyadenylation signal for polyadenylase. All of these regulatory regions should be capable of operating in the cells of the tissue to be transformed. Any suitable termination signal may be employed in carrying out the present invention, examples thereof including, but not limited to, the nos terminator, the CaMV terminator, or native termination signals derived from the same gene as the transcriptional initiation region or derived from a different gene. The term "operatively associated," as used herein, refers to DNA sequences on a single DNA molecule which are associated so that the function of one is affected by the other. Thus, a promoter is operatively associated with a DNA when it is capable of affecting the transcription of that DNA (i.e., the DNA is under the transcriptional control of the promoter). The promoter is said to be "upstream" from the DNA, which is in turn said to be "downstream" from the promoter.

The transcription cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; provide complementation, by imparting prototrophy to an auxotrophic host: or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are NPTII, providing kanamycin resistance or G418 resistance, HPT, providing hygromycin resistance, and the mutated aroA gene, providing glyphosate resistance.

The various fragments comprising the various constructs, transcription cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in J. Sambrook et al., Molecular Cloning, A Laboratory Manual (2d Ed. 1989)(Cold Spring Harbor Laboratory).

Vectors which may be used to transform plant tissue with DNA constructs of the present invention include both Agrobacterium vectors and ballistic vectors, as well as vectors suitable for DNA-mediated transformation.

Methods of making recombinant nematode-resistant plants of the invention, in general, involve providing a plant cell capable of regeneration (the plant cell typically residing in a tissue capable of regeneration). The plant cell is then transformed with a DNA construct comprising a transcription cassette of the present invention (as described herein) and a recombinant nematode-resistant plant regenerated from the transformed plant cell. As explained below, the transforming step is carried out by bombarding the plant cell with microparticles carrying the transcription cassette, by infecting the cell with an *Agrobacterium tumefaciens* containing a Ti plasmid carrying the transcription cassette, or any other technique suitable for the production of a transgenic plant.

Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T region, and a second plasmid having a T region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580. When using ballistic transformation procedures, the transcription cassette may be incorporated into a plasmid capable of replicating in or integrating into the cell to be transformed. Examples of microparticles suitable for use in such systems include 1 to 5 $\mu$m gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as nptII) can be associated with the transcription cassette to assist in breeding.

Some plants-parasitic nematodes from which plants may be protected by the present invention, and the corresponding plants which may be employed in practicing the present invention, are as follows: Alfalfa: *Ditylenchus dipsaci, Meloidogyne hapla, Meloidogyne incognita, Meloidogyne javanica*, Pratylenchus spp., Paratylenchus spp., and Xiphinema spp.; Banana: *Radopholus similis, Helicotylenchus multicinctus, Meloidogyne incognita, M. arenaria, M. javanica, Pratylenchus coffeae*, and *Rotylenchulus reniformis*; Beans & peas: Meloidogyne spp., Heterodera spp., Belonolaimus spp., Helicotylenchus spp., *Rotylenchulus reniformis, Paratrichodorus anemones*, and Trichodorus spp.; cassava: *Rotylenchulus reniformis*, Meloidogyne spp. cereals: *Anguina tritici* (Emmer, rye, spelt wheat), *Bidera avenae* (oat, wheat), *Ditylenchus dipsaci* (rye, oat), *Subanguina radicicola* (oat, barley, wheat, rye), *Meloidogyne naasi* (barley, wheat, rye), Pratylenchus spp. (oat, wheat, barley, rye), Paratylenchus spp. (wheat), Tylenchorhynchus spp. (wheat, oat); chickpea: *Heterodera cajani, Rotylenchulus reniformis, Hoplolaimus seinhorsti*, Meloidogyne spp., Pratylenchus spp.; Citrus: *Tylenchulus semipenetrans, Radopholus similis, Radopholus citrophilus* (Florida only), *Hemicycliophora arenaria*, Pratylenchus spp., Meloidogyne spp., *Bolonolaimus longicaudatus* (Florida only), Trichodorus, Paratrichodorus, Xiphinema spp.; clover: Meloidogyne spp., *Heterodera trifolii*; coconut: *Rhadinaphelenchus cocophilus*; coffee: *Meloidogyne incognita* (Most important in Brazil), *M. exigua* (widespread), *Pratylenchus coffeae, Pratylenchus brachyurus, Radopholus similis, Rotylenchulus reniformis*, Helicotylenchus spp.; corn: Pratylenchus spp., *Paratrichodorus minor*, Longidorus spp., *Hoplolaimus columbus*; cotton: *Meloidogyne incognita, Belonolaimus longicaudatus, Rotylenchulus reniformis, Hoplolaimus galeatus*, Pratylenchus spp., Tylenchorhynchus spp., *Paratrichodorus minor*; grapes: Xiphinema spp., *Pratylenchus vulnus*, Meloidogyne spp., *Tylenchulus semipenetrans, Rotylenchulus reniformis*; grasses: Pratylenchus spp., Longidorus spp., *Paratrichodorus christiei*, Xiphinema spp., Ditylenchus spp.; peanut: Pratylenchus spp., *Meloidogyne hapla., Meloidogyne arenaria*, Criconemella spp., *Belonolaimus longicaudatus* (in Eastern United States); pigeonpea: *Heterodera cajani, Rotylenchulus reniformis, Hoplolaimus seinhorsti*, Meloidogyne spp., Pratylenchus spp.; pineapple: *Paratrichodorus christiei*, Criconemella spp., Meloidogyne spp., *Rotylenchulus reniformis*, Helicotylenchus spp., Pratylenchus spp., Paratylenchus spp.; potato: *Globodera rostochiensis, Globodera pallida*, Meloidogyne spp., Pratylenchus spp., *Trichodorus primitivus*, Ditylenchus spp., Paratrichodorus spp., *Nacoabbus aberrans*; rice: *Aphelenchiodes besseyi, Ditylenchus angustus*, Hirchmanniella spp., *Heterodera oryzae*, Meloidogyne spp. small fruits: Meloidogyne spp.; Pratylenchus spp., Xiphinema spp., Longidorus spp., *Paratrichodorus christiei*, Aphelenchoides spp. (strawberry); soybean: *Heterodera glycines, Meloidogyne incognita, Meloidogyne javanica*, Belonolaimus spp., *Hoplolaimus columbus*; sugar beet: *Heterodera schachtii, Ditylenchus dipsaci*, Meloidogyne spp., *Nacobbus aberrans*, Trichodorus spp., Longidorus spp., Paratrichodorus spp.; sugar cane: Meloidogyne spp., Pratylenchus spp., Radopholus spp., Heterodera spp., Hoplolaimus spp., Helicotylenchus spp., Scutellonema spp., Belonolaimus spp., Tylenchorhynchus spp., Xiphinema spp., Longidorus spp., Paratrichodorus spp.; tea: Meloidogyne spp., Pratylenchus spp., *Radopholus similis, Hemicriconemoides kanayaensis*, Helicotylenchus spp., *Paratylenchus curvitatus*; tobacco: Meloidogyne spp., Pratylenchus spp., *Tylenchorhynchus claytoni, Globodera tabacum*, Trichodorus spp., *Xiphinema americanum, Ditylenchus dipsaci* (Europe only), Paratrichodorus spp.; tomato: Pratylenchus spp., Meloidogyne spp.; tree fruits: Pratylenchus spp. (apple, pear, stone fruits), Paratylenchus spp. (apple, pear), Xiphinema spp. (pear, cherry, peach), *Cacopaurus pestis* (walnut), Meloidogyne spp. (stone fruits, apple, etc.), Longidorus spp. (cherry), Criconemella spp. (peach), and Tylenchulus spp. (olive).

In view of the foregoing, it will be apparent that plants which may be employed in practicing the present invention include (but are not limited to) tobacco (*Nicotiana tabacum*), potato (*Solanum tuberosum*), soybean (glycine max), peanuts (*Arachis hypogaea*), cotton (*Gossypium hirsutum*), cassava (*Manihot esculenta*), coffee (Cofea spp.), coconut (*Cocos nucifera*), pineapple (*Ananas comosus*), citrus trees (Citrus spp.), banana (Musa spp.), corn (*Zea mays*), wheat, oats, rye, barley, rice, and vegetables such as green beans (*Phaseolus vulgaris*), lima beans (*Phaseolus limensis*), and peas (Lathyrus spp.). Thus, an illustrative category of plants which may be used to practice the present invention are the dicots, and a more particular category of plants which may be used to practice the present invention are the members of the family Solanacae.

In practice, a crop comprising a plurality of plants of the invention are planted together in an agricultural field. By "agricultural field", we mean a common plot of soil or a greenhouse, with the determinative feature typically being that a common population of nematodes infect that crop of plants. Thus, the present invention provides a method of combatting plant parasitic nematodes in an agricultural field, by planting the field with a crop of plants according to the invention.

The examples which follow are set forth to illustrate the present invention, and are not to be construed as limiting thereof.

EXAMPLE 1

Isolation and Expression of Genomic Root-Specific Clone RB7

*Nicotiana tabacum* cv Wisconsin 38 was used as the source of material for cloning and gene characterization. Genomic DNA was partially digested with Sau3A and size-fractionated on 5 to 20% potassium acetate gradients. Size fractions of 17 to 23 kb were pooled and ligated into the λ vector, EMBL3b that had been digested with BamHI and EcoRI. See A. Frischauf et al., J. Mol. Biol. 170, 827–842 (1983). A primary library of approximately $3.5 \times 10^6$ recombinants was screened by plaque hybridization. Positive clones were plaque purified. Restriction maps of the genomic clones were constructed using the rapid mapping procedure of Rachwitz et al., Gene 30, 195–200 (1984).

Regions encoding the root-specific clones were identified by Southern blots. To further define the transcribed regions, we took advantage of the fact that the genes are expressed at high levels. Thus, probes made of cDNA of reverse transcribed poly(A+)RNA would hybridize to Southern blots of restricted genomic clones in a manner analogous to differential screening experiments. See F. Kilcherr, Nature 321, 493–499 (1986). The clones were digested with the appropriate restriction enzymes and the fragments separated on agarose gels. These fragments were then Southern blotted to nitrocellulose filters and probed with reverse transcribed root poly(A+)RNA. The probe was primed using random hexanucleotides (Pharmacia Biochemicals, Inc.) such that the 3' termini of the mRNA molecules would not be over represented among the probe.

Clones hybridizing to each root-specific cDNA clone were plaque purified. Comparisons of the restriction maps of the genomic clones with genomic Southern hybridization experiments (not shown) reveal a good correlation of the sequences hybridizing to the root-specific cDNA clones. Clone λ5A hybridized to the cDNA clone TobRB7. This appears to be the genomic clone corresponding to TobRB7 and accordingly was designated as TobRB7-5A (SEQ ID NO:6) and used to generate the promoter sequences employed in the experiments described below. The cell membrane channel protein is set forth as SEQ ID NO:7.

EXAMPLE 2

Identification of a Nematode-Responsive Element Within the TobRB7 Promoter

The ability of the TobRB7 promoter region of the λ5A genomic clone to regulate the expression of a heterologous reporter gene was tested by cloning approximately 1.4 kb of 5' flanking sequence into pBI101.2 The length of the TobRB7 flanking region employed was varied to explore how various portions of the flanking region affected expression of GUS.

In brief, a TobRB7 5' flanking region was isolated from λ5A and fused with β-glucuronidase in the Agrobacterium binary vector, pBI 101.2. This vector contains a β-glucuronidase (GUS) reporter gene and an nptII selectable marker flanked by the T-DNA border sequences (R. Jefferson et al., *EMBO J.* 6, 3901–3907 (1987)). The TobRB7 structural gene was completely removed and the TobRB7 flanking regions fused to the GUS initiating methionene codon. The construction was mobilized into an Agrobacterium host that carries a disarmed Ti-plasmid (LBA4404) capable of providing (in trans) the vir functions required for T-DNA transfer and integration into the plant genome, essentially as described by An et al., in S. Belvin and R. Schilperoot, eds., Plant Molecular Biology Manual, Martinus Nijhoff, Dordrecht, The Netherlands, pp A3-1-19 (1988). *Nicotiana tabacum* SR1 leaf discs were infected and transformants selected and regenerated as described by An et al., *Plant Physiol.* 81, 301–305 (1986).

Whole plants or excised root and leaf tissue were assayed for GUS expression according to Jefferson et al., supra. For histochemical staining, plants were incubated in the 5-bromo-4-chloro-3-indolyl β-D-glucuronide (X-GLUC) at 37° C. overnight. Tissues expressing GUS activity cleave this substrate and thereby stain blue. After the incubation the tissues were bleached in 70% ethanol. GUS enzyme activities were measured using the fluorogenic assay described by Jefferson et al.

The activity of the various deletion mutants was tested. The greatest root-specific gene expression was obtained with the Δ0.6 deletion mutant (SEQ ID NO:4). Only the Δ0.3 deletion mutant (SEQ ID NO:5) was inactive as a promoter, indicating that the TobRB7 promoter is found in the region extending about 800 nucleotides upstream from the TobRB7 structural gene. However, the Δ0.3 deletion mutant (SEQ ID NO:5) contains the RB7 nematode-responsive element, as discussed below.

EXAMPLE 3

Localization of Gene Activation in Nematode Infected Plants

Transgenic tobacco plants prepared as described in Example 2 above were infected with tobacco root-knot nematodes (*Meloidogyne incognita*) in accordance with known techniques. See, e.g., C. Opperman et al., *Plant Disease,* 869–871 (October 1988). Roots were stained for GUS activity (blue) and nematodes were stained red at three stages: (a) 24–48 hours post infection; (b) 7–10 days post infection; and (c) 20–25 days post infection. Nematodes were stained after GUS staining by incubating roots in 95% ethanol/glacial acetic acid (1:1) plus five drops of acid fushsin (per 100 mLs) for four hours, then destained in a saturated chloral hydrate solution for twelve hours to overnight.

GUS activity was generally found in the elongation zone of the root. At 24–48 hours post infection, second stage juvenile nematodes have penetrated the tobacco roots, are in the corticle tissue and are migrating in search of an appropriate feeding site. Juveniles in the vascular tissue at this stage have already begun to establish feeding sites. At 7–10 days post infection, swollen late second stage juveniles are seen with their heads in the feeding site. At 20–25 days post infection, adult nematodes are seen protruding from galled root tissue, with their head still embedded in the vascular tissue and the posterior exposed to allow egg deposition.

GUS activity in nematode infected root tissue of plants transformed with the various deletion mutants described in Example 2 indicated that the nematode-responsive element of the TobRB7 promoter is located in the Δ0.3 (SEQ ID NO:5) deletion mutant.

Similar results are obtained with the peanut root-knot nematode (*Meloidogyne arenaria*).

During the foregoing experiments, it was observed that duration of gene expression in nematode-infected plants was much longer than in uninfected plants, and that the regions of gene activity were no longer restricted to the elongation zone of the root. For example, in each location where a nematode was able to establish a feeding site, gene expression continued at that site for as long as 25–30 days (i.e., the duration of the nematode life cycle).

EXAMPLE 4

Inhibition of Nematode Feeding Site Formation by Expression of Sense or Antisense TobRB7 mRNA This example demonstrates the ability of transgenic plants expressing sense and anti-sense TobRB7 mRNA under the control of a constitutively active promoter to interfere with the establishment of root-knot nematode feeding sites. The constructions employed are described in FIG. 1, and the plants were prepared in essentially the same manner as described in Example 2 above. The sense DNA employed had the sequence given herein as SEQ ID NO:1, and the antisense DNA employed had the sequence given herein as SEQ ID NO:3. The promoter employed was the Cauliflower Mosaic Virus 35S promoter, and the termination signal employed was the nos terminator. The constructs were transferred to the Agrobacterium binary vector pBIN19 and transgenic plants were produced in essentially the same manner as described above: tobacco leaf disks were transformed and transformants selected on kanamycin; regenerants were allowed to self and set seeds; seeds (R2) were germinated on kanamycin and segregation of the Kan$^r$ marker assayed; those plants exhibiting a 3:1 segregation (i.e., containing a single locus of integration) were allowed to self; progeny of the R2 were germinated on kanamycin to determine those R2 progeny that were homozygous for the transgene.

The phenotypes of a large number of control, sense, and antisense plants were examined. Control plants looked like normal tobacco. Sense and antisense plants exhibited similar phenotypes: (1) long internodes, (2) narrow and pointed leaves, and (3) early flowering. These phenotypes resemble "stress" phenotypes exhibited by plants grown in suboptimal conditions, such as small pots. It appears that the "stress" phenotype in sense plants results from the phenomenon of co-suppression: a phenomenon in which plants carrying transgenes in the sense orientation show reduced, rather than increased, levels of gene expression. See, e.g., C. Napoli et al., *The Plant Cell* 2, 279–289 (1990).

Transgenic plants of sense transformants, anti-sense transformants, and control transformants were infected with second-stage juveniles of *M. arenaria* in essentially the same manner as described above. Approximately 100,000 nematodes suspended in sterile water were pipetted along the roots of plants growing on agar plates. Plants were maintained in a growth chamber at 25° C. At 24 hr post infection, juveniles were observed in various stages of root penetration on all plates. Galls were visible on all treatments by 3–5 days post infection.

Roots were harvested from plates 2A, 2B, and 7 (anti-sense); 13 and 37 (sense); and 22A and 22B (control) at 21 days post-infection. Initial observations revealed substantial and extensive galling of the sense and control plants. Galls often appeared in clusters along the root. It appeared that in a number of galls, adult female nematodes had begun reproduction. In contrast, few galls were present on the anti-sense plants. Those that were present occurred singly rather than in clusters and were substantially reduced in size compared to the sense and control plants (<50% the diameter). Two of the three plates yielded no plants with visible galling at 21 days post-infection.

Roots from each treatment were stained with acid fuchsin to determine stage of nematode development and the degree of root penetration. Roots of sense and control plants were infected with numerous nematodes in various stages of development. Mature females were observed in several galls and egg production appeared to have been initiated. Galls contained numerous nematodes. Other stages observed included vermiform second-stage juveniles, swollen second-stage juveniles, and third/fourth stage juveniles. No adult males were observed within roots or on plates. Far fewer nematodes were observed in anti-sense plants. Those that were present were mostly veriform or swollen second-stage juveniles. No adult female nematodes were found. Several adult male nematodes were observed within the roots, but not on the plate surface. Galls that were present generally contained a single nematode and tended to occur at root junctions.

EXAMPLE 5

Effect on Nematode Nematode Egg Mass Rating of Expression of Sense or Antisense TobRB7 mRNA under the Control of a Constitutive Promoter Transgenic tobacco plants expressing sense or antisense TobRB7 mRNA prepared as described above were infected with tobacco root-knot nematodes (*Meloidogyne incognita*) in accordance with known techniques. See, e.g., C. Opperman et al., *Plant Disease*, 869–871 (October 1988). 63 days after infection, roots were harvested, egg masses were stained with Phloxine B to facilitate counting in accordance with known techniques and egg masses counted. Both sense and antisense plants were found resistant to nematodes. These data are given in Table 1 below.

TABLE 1

Egg Mass Ratings at 63 Days After Infection

| Transformant Line | Egg Mass Rating | Number of Eggs | Plant Type |
| --- | --- | --- | --- |
| 37 | 2.6 ± 0.5 | 1120 | sense |
| 6 | 3.6 ± 1.0 | 3516 | antisense |
| 20 | 3.8 ± 1.3 | 3270 | antisense |
| 2 | 4.0 ± 1.0 | NA | antisense |
| 13 | 4.3 ± 0.5 | 5400 | sense |
| 34 | 4.4 ± 0.7 | 4594 | sense |
| 36 | 4.5 ± 0.8 | 6980 | sense |
| 21 | 4.6 ± 0.5 | 5300 | control |
| 22 | 4.7 ± 0.5 | 6000 | control |

Egg Mass Rating: 0 = no egg masses; 1 = <10 egg masses; 2 = 10–50 egg masses; 3 = 50–150 egg masses; 4 = 150–300 egg masses; 5 = >300 egg masses.
NA = not available.

EXAMPLE 6

Figure 2:
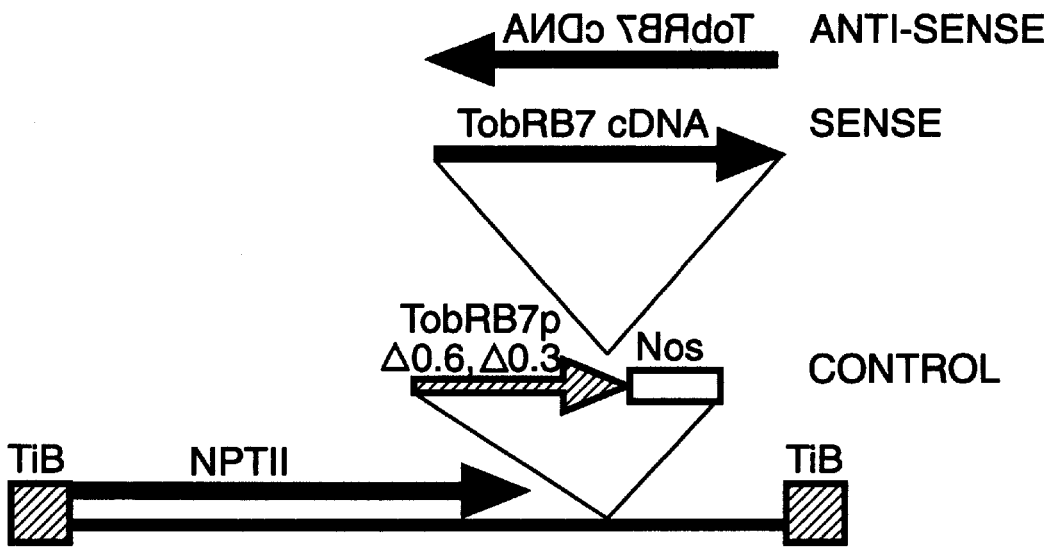
FIG. 2 illustrates transcription cassettes much like those illustrated in FIG. 1 above, except that the constitutively active CaMV35S promoter is replaced with either the element TobRB7 Δ0.6 which is selectively active in root tissue cells or the nematode-responsive element TobRB7 Δ0.3.

Inhibition of Nematode Feeding site Formation by Expression of Sense or Antisense TobRB7 mRNA under the Control of a Nematode-Responsive Element or a Root-Specific Gene Promoter Transgenic plants expressing sense anti-sense TobRB7 mRNA under the control of a promoter comprising a root specific gene promoter or a nematode-responsive element interfere with the establishment of root-knot nematode feeding sites. The constructions employed are described in FIG. 2. Sense, antisense, and control plants were produced in essentially the same manner as described in Example 4 above, except that the root specific promoter described above and having the sequence given in SEQ ID NO:4 was employed in place of the CaMV 35S promoter. Additionally, sense, antisense, and control plants were produced in essentially the same manner as described in Example 4 above, except that the nematode-responsive element described above and having the sequence given herein as SEQ ID NO:5 was employed in place of the CaMV 35S promoter. Resistance to nematodes is shown in the same manner as described above.

The foregoing examples are illustrative of the present invention, and are not to be construed as limiting thereof. The invention is defined by the following claims, with equivalents of the claims to be included therein.

That which is claimed is:

1. A DNA construct comprising a transcription cassette, which construct comprises, in the 5' to 3' direction, a promoter operable in a plant cell, and a DNA segment comprising at least 15 nucleotides of a DNA sequence encoding a nematode-inducible transmembrane pore protein, said DNA segment in the opposite orientation for expression, where said DNA sequence encoding a nematode-inducible transmembrane pore protein is selected from the group consisting of:

(a) isolated DNA having the sequence given herein as SEQ ID NO:1 or SEQ ID NO:6;
   (b) isolated DNA which hybridizes to isolated DNA of (a) above and which encodes a nematode inducible transmembrane pore protein; and
   (c) isolated DNA differing from the isolated DNA of (a) and (b) above in nucleotide sequence due to the degeneracy of the genetic code, and which encode a nematode-inducible transmembrane pore protein.

2. A DNA construct according to claim 1, which DNA sequence encoding a nematode-inducible transmembrane pore protein encodes a TobRB7 nemtode-inducible transmembrane pore protein.

3. A DNA construct according to claim 1, which DNA segment in the opposite orientation for expression includes an intron-exon junction.

4. A DNA construct according to claim 1, which DNA segment in the opposite orientation for expression has SEQ ID NO:3.

5. A DNA construct according to claim 1, which promoter is constitutively active in plant cells.

6. A DNA construct according to claim 1, which promoter is selectively active in plant root tissue cells.

7. A DNA construct according to claim 1, which promoter is a Cauliflower Mosaic Virus 35S promoter.

8. A DNA construct according to claim 1, which promoter is activated by a plant-parasitic nematode.

9. A DNA construct according to claim 1, which promoter is a nematode-responsive element selected from the group consisting of:

(i) isolated DNA having the sequence given herein as SEQ ID NO:5; and
   (ii) isolated DNA which hybridizes to isolated DNA of (i) above and which encodes a nematode responsive element.

10. A DNA construct according to claim 1, which promoter is an RB7 nematode-responsive element.

11. A DNA construct according to claim 1 carried by a plant transformation vector.

12. A DNA construct according to claim 1 carried by a plant transformation vector, which plant transformation vector is an *Agrobacterium tumefaciens* vector.

13. A nematode-resistant transgenic plant comprising plant cells containing a DNA construct comprising a transcription cassette, which construct comprises, in the 5' to 3' direction, a promoter operable in said plant cells, and a DNA segment comprising at least 15 nucleotides of a DNA sequence encoding a nematode-inducible transmembrane pore protein, said DNA segment in the opposite orientation for expression, where said DNA sequence encoding a nematode-inducible transmembrane pore protein is selected from the group consisting of:

(a) isolated DNA having the sequence given herein as SEQ ID NO:1 or SEQ ID NO:6;

(b) isolated DNA which hybridizes to isolated DNA of (a) above and which encodes a nematode inducible transmembrane pore protein; and (c) isolated DNA differing from the isolated DNAs of (a) and (b) above in nucleotide sequence due to the degeneracy of the genetic code, and which encode a nematode-inducible transmembrane pore protein.

14. A plant according to claim 13, which plant is a dicot.

15. A plant according to claim 13, which plant is a dicot selected from the group consisting of tobacco, potato, soybean, peanuts, pineapple, and cotton.

16. A plant according to claim 13, which plant is a member of the family Solanacae.

17. A plant according to claim 13, which DNA sequence encoding a nematode-inducible transmembrane pore protein encodes a TobRB7 nematode-inducible transmembrane pore protein is selected from the group consisting of:

(a) isolated DNA having the sequence given herein as SEQ ID NO:1 or SEQ ID NO:6;

(b) isolated DNA which hybridizes to isolated DNA of (a) above and which encodes a nematode inducible transmembrane pore protein; and (c) isolated DNA differing from the isolated DNAs of (a) and (b) above in nucleotide sequence due to the degeneracy of the genetic code, and which encode a nematode-inducible transmembrane pore protein.

18. A plant according to claim 13, which promoter is constitutively active in plant cells.

19. A plant according to claim 13, which promoter is selectively active in plant root tissue cells.

20. A plant according to claim 13, which promoter is activated by a plant-parasitic nematode.

21. A plant according to claim 13, which promoter is a nematode-responsive element selected from the group consisting of:

(i) isolated DNA having the sequence given herein as SEQ ID NO:5; and (ii) isolated DNA which hybridizes to isolated DNA of (i) above and which encodes a nematode responsive element.

22. A crop comprising a plurality of plants according to claim 13 planted together in an agricultural field.

23. A method of combatting plant parasitic nematodes in an agricultural field, comprising planting the field with a crop of plants according to claim 13.

24. A method of making a recombinant pathogen-resistant plant, said method comprising:

providing a plant cell capable of regeneration;

transforming said plant cell with a DNA construct comprising a transcription cassette, which construct comprises, in the 5' to 3' direction, a promoter operable in said plant cell, and a DNA segment comprising at least 15 nucleotides of a DNA sequence encoding a nematode-inducible transmembrane pore protein, said DNA segment in either (a) the opposite orientation for expression or (b) the proper orientation for expression, and where said DNA sequence encoding a nematode-inducible transmembrane pore protein is selected from the group consisting of:

(a) isolated DNA having the sequence given herein as SEQ ID NO:1 or SEQ ID NO:6;

(b) isolated DNA which hybridizes to isolated DNA of (a) above and which encodes a nematode inducible transmembrane pore protein; and (c) isolated DNA differing from the isolated DNAs of (a) and (b) above in nucleotide sequence due to the degeneracy of the genetic code, and which encode a nematode-inducible transmembrane pore protein; and then regenerating a recombinant nematode-resistant plant from said transformed plant cell.

25. A method according to claim 24, wherein said plant cell resides in a plant tissue capable of regeneration.

26. A method according to claim 24, wherein said transforming step is carried out by bombarding said plant cell with microparticles carrying said transcription cassette.

27. A method according to claim 24, wherein said transforming step is carried out by infecting said cells with an *Agrobacterium tumefaciens* containing a Ti plasmid carrying said transcription cassette.

28. A nematode-resistant transgenic plant comprising plant cells containing a heterologous DNA construct comprising a transcription cassette, which heterologous construct comprises in the 5' to 3' direction, a promoter operable in said plant cells, and a DNA segment comprising at least 15 nucleotides of a DNA sequence encoding a nematode-inducible transmembrane pore protein, said DNA segment in the proper orientation for expression, and where said DNA sequence encoding a nematode-inducible transmembrane pore protein is selected from the group consisting of:

(a) isolated DNA having the sequence given herein as SEQ ID NO:1 or SEQ ID NO:6;

(b) isolated DNA which hybridizes to isolated DNA of (a) above and which encodes a nematode inducible transmembrane pore protein; and (c) isolated DNA differing from the isolated DNAs of (a) and (b) above in nucleotide sequence due to the degeneracy of the genetic code, and which encode a nematode-inducible transmembrane pore protein.

29. A plant according to claim 28, which plant is a dicot.

30. A plant according to claim 28, which plant is a dicot selected from the group consisting of tobacco, potato, soybean, peanuts, pineapple, and cotton.

31. A plant according to claim 28, which plant is a member of the family Solanacae.

32. A plant according to claim 28, which DNA sequence encoding a nematode-inducible transmembrane pore protein encodes a TobRB7 nematode-inducible transmembrane pore protein is selected from the group consisting of:

(a) isolated DNA having the sequence given herein as SEQ ID NO:1 or SEQ ID NO:6;

(b) isolated DNA which hybridizes to isolated DNA of (a) above and which encodes a nematode inducible transmembrane pore protein; and (c) isolated DNA differing from the isolated DNAs of (a) and (b) above in nucleotide sequence due to the degeneracy of the genetic code, and which encode a nematode-inducible transmembrane pore protein.

33. A plant according to claim 28, which DNA segment comprising at least 15 nucleotides of a DNA sequence encoding a nematode-inducible transmembrane pore protein is a sense DNA segment in the proper orientation for expression.

34. A plant according to claim 28, which DNA segment comprising at least 15 nucleotides of a DNA sequence encoding a nematode-inducible transmembrane pore protein is an antisense DNA segment in the opposite orientation for expression.

35. A plant according to claim 28, which promoter is constitutively active in plant cells.

36. A plant according to claim 28, which promoter is selectively active in plant root tissue cells.

37. A plant according to claim 28, which promoter is activated by a plant-parasitic nematode.

38. A plant according to claim 28, which promoter is a nematode-responsive element selected from the group consisting of:
(i) isolated DNA having the sequence given herein as SEQ ID NO:5; and
(ii) isolated DNA which hybridizes to isolated DNA of (i) above and which encodes a nematode responsive element.

39. A crop comprising a plurality of nematode-resistant transgenic plants planted together in an agricultural field, said nematode-resistant transgenic plants comprising plant cells, said plant cells containing a DNA construct comprising a transcription cassette, which construct comprises, in the 5' to 3' direction, a promoter operable in said plant cells, and a DNA segment comprising at least 15 nucleotides of a DNA sequence encoding a nematode-inducible transmembrane pore protein, said DNA segment in the proper orientation for expression, and where said DNA sequence encoding a nematode-inducible transmembrane pore protein is selected from the group consisting of:
(a) isolated DNA having the sequence given herein as SEQ ID NO:1 or SEQ ID NO:6;
(b) isolated DNA which hybridizes to isolated DNA of (a) above and which encodes a nematode inducible transmembrane pore protein; and
(c) isolated DNA differing from the isolated DNAs of (a) and (b) above in nucleotide sequence to the degeneracy of the genetic code, and which encode a nematode-inducible transmembrane pore protein.

40. A method of combatting plant parasitic nematodes in an agricultural field, comprising planting the field with a crop of nematode-resistant transgenic plants comprising plant cells, said plant cells containing a DNA construct comprising a transcription cassette, which construct comprises, in the 5' to 3' direction, a promoter operable in said plant cells, and a DNA segment comprising at least 15 nucleotides of a DNA sequence encoding a nematode-inducible transmembrane pore protein, said DNA segment in the proper orientation for expression, where said DNA sequence encoding a nematode-inducible transmembrane pore protein is selected from the group consisting of:
(a) isolated DNA having the sequence given herein as SEQ ID NO:1 or SEQ ID NO:6;
(b) isolated DNA which hybridizes to isolated DNA of (a) above and which encodes a nematode inducible transmembrane pore protein; and
(c) isolated DNA differing from the isolated DNAs of (a) and (b) above in nucleotide sequence due to the degeneracy of the genetic code, and which encode a nematode-inducible transmembrane pore protein.

41. A transgenic tobacco plant comprising tobacco plant cells containing a heterologous DNA construct comprising a transcription cassette, which construct comprises, in the 5' to 3' direction, a promoter operable in said tobacco plant cells, and a heterologous DNA sequence encoding a nematode-inducible transmembrane pore protein;
said promoter selected from the group consisting of the Cauliflower Mosaic Virus 35S promoter and the promoter encoded by SEQ ID NO:5;
said heterologous DNA sequence selected from the group consisting of DNA having the sequence given herein as SEQ ID NO:1, SEQ ID NO:3, and SEQ ID NO:6;
said tobacco plant resistant to a nematode selected from the group consisting of *Meloidogyne incognita* and *Meloidogyne arenaria*.

42. A DNA construct comprising a transcription cassette, which construct comprises, in the 5' to 3' direction, a promoter operable in a plant cell, and a DNA segment comprising at least 15 nucleotides of a DNA sequence encoding a nematode-inducible transmembrane pore protein, said DNA segment in the proper orientation for expression, where said DNA sequence encoding a nematode-inducible transmembrane pore protein is selected from the group consisting of:
(a) isolated DNA having the sequence given herein as SEQ ID NO:1 or SEQ ID NO:6;
(b) isolated DNA which hybridizes to isolated DNA of (a) above and which encodes a nematode inducible transmembrane pore protein; and
(c) isolated DNA differing from the isolated DNAs of (a) and (b) above in nucleotide sequence due to the degeneracy of the genetic code, and which encode a nematode-inducible transmembrane pore protein.

43. A DNA construct according to claim 42, which DNA sequence encoding a nematode-inducible transmembrane pore protein encodes a TobRB7 nematode-inducible transmembrane pore protein is selected from the group consisting of:
(a) isolated DNA having the sequence given herein as SEQ ID NO:1 or SEQ ID NO:6;
(b) isolated DNA which hybridizes to isolated DNA of (a) above and which encodes a nematode inducible transmembrane pore protein; and
(c) isolated DNA differing from the isolated DNAs of (a) and (b) above in nucleotide sequence due to the degeneracy of the genetic code, and which encode a nematode-inducible transmembrane pore protein.

44. A DNA construct according to claim 42, which DNA segment includes an intron-exon junction.

45. A DNA construct according to claim 42, which DNA segment has SEQ ID NO:3.

46. A DNA construct according to claim 42, which promoter is constitutively active in plants.

47. A DNA construct according to claim 42, which promoter is selectively active in plant root tissue cells.

48. A DNA construct according to claim 42, which promoter is a Cauliflower Mosaic Virus 35S promoter.

49. A DNA construct according to claim 42, which promoter is activated by a plant-parasitic nematode.

50. A DNA construct according to claim 42, which promoter is a nematode-responsive element selected from the group consisting of:
(i) isolated DNA having the sequence given herein as SEQ ID NO:5;
(ii) isolated DNA which hybridizes to isolated DNA of (i) above and which encodes a nematode responsive element.

51. A DNA construct according to claim 42, which promoter is an RB7 nematode-responsive element.

52. A DNA construct according to claim 42 carried by a plant transformation vector.

53. A DNA construct according to claim 42 carried by a plant transformation vector, which plant transformation vector is an *Agrobacterium tumefaciens* vector.

* * * * *

UNITED STATES PATENT AND TRADEMARK OFFICE
CERTIFICATE OF CORRECTION

PATENT NO.    : 6,008,436
DATED         : December 28, 1999
INVENTOR(S)   : Conkling et al.

It is certified that error appears in the above-identified patent and that said Letters Patent is hereby corrected as shown below:

Column 29,
Line 17, should read -- protein. -- The remainder of line 17 through line 26 should be deleted.

Column 30,
Line 43, should read -- protein. -- The remainder of line 43 through line 52 should be deleted.

Column 32,
Line 5, should read -- membrane pore protein. -- the remainder of line 25 through line 35 should be deleted.

Signed and Sealed this

Sixth Day of July, 2004

JON W. DUDAS
*Acting Director of the United States Patent and Trademark Office*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 938 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 47..799

(ix) FEATURE:
    (A) NAME/KEY: mat_peptide
    (B) LOCATION: 47..796

(xi) SEQUENCE DESCRIPTION: SEQ ID NO:1:

```
CTTAAATTGA GCTTCTTTTG GGGCATTTTT CTAGTGAGAA CTAAAA ATG GTG AGG          55
                                                  Met Val Arg
                                                   1

ATT GCC TTT GGT AGC ATT GGT GAC TCT TTT AGT GTT GGA TCA TTG AAG        103
Ile Ala Phe Gly Ser Ile Gly Asp Ser Phe Ser Val Gly Ser Leu Lys
     5                  10                  15

GCC TAT GTA GCT GAG TTT ATT GCT ACT CTT CTC TTT GTG TTT GCT GGG        151
Ala Tyr Val Ala Glu Phe Ile Ala Thr Leu Leu Phe Val Phe Ala Gly
 20              25                  30                  35

GTT GGG TCT GCT ATA GCT TAT AAT AAA TTG ACA GCA GAT GCA GCT CTT        199
Val Gly Ser Ala Ile Ala Tyr Asn Lys Leu Thr Ala Asp Ala Ala Leu
             40                  45                  50

GAT CCA GCT GGT CTA GTA GCA GTA GCT GTG GCT CAT GCA TTT GCA TTG        247
Asp Pro Ala Gly Leu Val Ala Val Ala Val Ala His Ala Phe Ala Leu
                 55                  60                  65

TTT GTT GGG GTT TCC ATA GCA GCC AAT ATT TCA GGT GGC CAT TTG AAT        295
Phe Val Gly Val Ser Ile Ala Ala Asn Ile Ser Gly Gly His Leu Asn
                     70                  75                  80

CCA GCT GTC ACT TTG GGA TTG GCT GTT GGT GGA AAC ATC ACC ATC TTG        343
Pro Ala Val Thr Leu Gly Leu Ala Val Gly Gly Asn Ile Thr Ile Leu
 85                  90                  95

ACT GGC TTC TTC TAC TGG ATT GCC CAA TTG CTT GGC TCC ACA GTT GCT        391
Thr Gly Phe Phe Tyr Trp Ile Ala Gln Leu Leu Gly Ser Thr Val Ala
100                 105                 110                 115

TGC CTC CTC CTC AAA TAC GTT ACT AAT GGA TTG GCT GTT CCA ACC CAT        439
Cys Leu Leu Leu Lys Tyr Val Thr Asn Gly Leu Ala Val Pro Thr His
                120                 125                 130

GGA GTT GCT GCT GGG CTC AAT GGA TTA CAA GGA GTG GTG ATG GAG ATA        487
Gly Val Ala Ala Gly Leu Asn Gly Leu Gln Gly Val Val Met Glu Ile
                135                 140                 145

ATC ATA ACC TTT GCA CTG GTC TAC ACT GTT TAT GCA ACA GCA GCA GAC        535
Ile Ile Thr Phe Ala Leu Val Tyr Thr Val Tyr Ala Thr Ala Ala Asp
            150                 155                 160

CCT AAA AAG GGC TCA CTT GGA ACC ATT GCA CCC ATT GCA ATT GGG TTC        583
Pro Lys Lys Gly Ser Leu Gly Thr Ile Ala Pro Ile Ala Ile Gly Phe
165                 170                 175

ATT GTT GGG GCC AAC ATT TTG GCA GCT GGT CCA TTC AGT GGT GGG TCA        631
Ile Val Gly Ala Asn Ile Leu Ala Ala Gly Pro Phe Ser Gly Gly Ser
180                 185                 190                 195

ATG AAC CCA GCT CGA TCA TTT GGG CCA GCT GTG GTT GCA GGA GAC TTT        679
Met Asn Pro Ala Arg Ser Phe Gly Pro Ala Val Val Ala Gly Asp Phe
                200                 205                 210

TCT CAA AAC TGG ATC TAT TGG GCC GGC CCA CTC ATT GGT GGA GGA TTA        727
Ser Gln Asn Trp Ile Tyr Trp Ala Gly Pro Leu Ile Gly Gly Gly Leu
                215                 220                 225

GCT GGG TTT ATT TAT GGA GAT GTC TTT ATT GGA TGC CAC ACC CCA CTT        775
Ala Gly Phe Ile Tyr Gly Asp Val Phe Ile Gly Cys His Thr Pro Leu
            230                 235                 240

CCA ACC TCA GAA GAC TAT GCT TAAAACTTAA AAGAAGACAA GTCTGTCTTC           826
Pro Thr Ser Glu Asp Tyr Ala
245                 250

AATGTTTCTT TGTGTGTTTT CAAATGCAAT GTTGATTTTT AATTTAAGCT TTGTATATTA      886

TGCTATGCAA CAAGTTTGTT TCCAATGAAA TATCATGTTT TGGTTTCTTT TG              938
```

(2) INFORMATION FOR SEQ ID NO:2:

(i) SEQUENCE CHARACTERISTICS:
        (A) LENGTH: 250 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Arg Ile Ala Phe Gly Ser Ile Gly Asp Ser Phe Ser Val Gly
 1               5                  10                  15

Ser Leu Lys Ala Tyr Val Ala Glu Phe Ile Ala Thr Leu Leu Phe Val
                20                  25                  30

Phe Ala Gly Val Gly Ser Ala Ile Ala Tyr Asn Lys Leu Thr Ala Asp
            35                  40                  45

Ala Ala Leu Asp Pro Ala Gly Leu Val Ala Val Ala Val Ala His Ala
        50                  55                  60

Phe Ala Leu Phe Val Gly Val Ser Ile Ala Ala Asn Ile Ser Gly Gly
65                  70                  75                  80

His Leu Asn Pro Ala Val Thr Leu Gly Leu Ala Val Gly Gly Asn Ile
                85                  90                  95

Thr Ile Leu Thr Gly Phe Phe Tyr Trp Ile Ala Gln Leu Leu Gly Ser
                100                 105                 110

Thr Val Ala Cys Leu Leu Leu Lys Tyr Val Thr Asn Gly Leu Ala Val
            115                 120                 125

Pro Thr His Gly Val Ala Ala Gly Leu Asn Gly Leu Gln Gly Val Val
        130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
                180                 185                 190

Gly Gly Ser Met Asn Pro Ala Arg Ser Phe Gly Pro Ala Val Val Ala
            195                 200                 205

Gly Asp Phe Ser Gln Asn Trp Ile Tyr Trp Ala Gly Pro Leu Ile Gly
        210                 215                 220

Gly Gly Leu Ala Gly Phe Ile Tyr Gly Asp Val Phe Ile Gly Cys His
225                 230                 235                 240

Thr Pro Leu Pro Thr Ser Glu Asp Tyr Ala
                245                 250
```

(2) INFORMATION FOR SEQ ID NO:3:

(i) SEQUENCE CHARACTERISTICS:
        (A) LENGTH: 938 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:3:

```
CAAAAGAAAC CAAAACATGA TATTTCATTG GAAACAAACT TGTTGCATAG CATAATATAC      60

AAAGCTTAAA TTAAAATCA ACATTGCATT TGAAACACA CAAAGAAACA TTGAAGACAG       120

ACTTGTCTTC TTTTAAGTTT TAAGCATAGT CTTCTGAGGT TGGAAGTGGG GTGTGGCATC     180
```

| | |
|---|---|
| CAATAAAGAC ATCTCCATAA ATAAACCCAG CTAATCCTCC ACCAATGAGT GGGCCGGCCC | 240 |
| AATAGATCCA GTTTTGAGAA AAGTCTCCTG CAACCACAGC TGGCCCAAAT GATCGAGCTG | 300 |
| GGTTCATTGA CCCACCACTG AATGGACCAG CTGCCAAAAT GTTGGCCCCA ACAATGAACC | 360 |
| CAATTGCAAT GGGTGCAATG GTTCCAAGTG AGCCCTTTTT AGGGTCTGCT GCTGTTGCAT | 420 |
| AAACAGTGTA GACCAGTGCA AAGGTTATGA TTATCTCCAT CACCACTCCT TGTAATCCAT | 480 |
| TGAGCCCAGC AGCAACTCCA TGGGTTGGAA CAGCCAATCC ATTAGTAACG TATTTGAGGA | 540 |
| GGAGGCAAGC AACTGTGGAG CCAAGCAATT GGGCAATCCA GTAGAAGAAG CCAGTCAAGA | 600 |
| TGGTGATGTT TCCACCAACA GCCAATCCCA AAGTGACAGC TGGATTCAAA TGGCCACCTG | 660 |
| AAATATTGGC TGCTATGGAA ACCCCAACAA ACAATGCAAA TGCATGAGCC ACAGCTACTG | 720 |
| CTACTAGACC AGCTGGATCA AGAGCTGCAT CTGCTGTCAA TTTATTATAA GCTATAGCAG | 780 |
| ACCCAACCCC AGCAAACACA AAGAGAAGAG TAGCAATAAA CTCAGCTACA TAGGCCTTCA | 840 |
| ATGATCCAAC ACTAAAAGAG TCACCAATGC TACCAAAGGC AATCCTCACC ATTTTTAGTT | 900 |
| CTCACTAGAA AAATGCCCCA AAAGAAGCTC AATTTAAG | 938 |

(2) INFORMATION FOR SEQ ID NO:4:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

| | |
|---|---|
| GTCCTACACA ATGTGAATTT GAATTAGTTT GGTCATACGG TATATCATAT GATTATAAAT | 60 |
| AAAAAAAATT AGCAAAAGAA TATAATTTAT TAAATATTTT ACACCATACC AAACACAACC | 120 |
| GCATTATATA TAATCTTAAT TATCATTATC ACCAGCATCA ACATTATAAT GATTCCCCTA | 180 |
| TGCGTTGGAA CGTCATTATA GTTATTCTAA ACAAGAAAGA AATTTGTTCT TGACATCAGA | 240 |
| CATCTAGTAT TATAACTCTA GTGGAGCTTA CCTTTTCTTT TCCTTCTTTT TTTTCTTCTT | 300 |
| AAAAAAATTA TCACTTTTTA AATCTTGTAT ATTAGTTAAG CTTATCTAAA CAAAGTTTTA | 360 |
| AATTCATTTC TTAAACGTCC ATTACAATGT AATATAACTT AGTCGTCTCA ATTAAACCAT | 420 |
| TAATGTGAAA TATAAATCAA AAAAAGCCAA AGGGCGGTGG GACGGCGCCA ATCATTTGTC | 480 |
| CTAGTCCACT CAAATAAGGC CCATGGTCGG CAAAACCAAA CACAAAATGT GTTATTTTTA | 540 |
| ATTTTTTCCT CTTTTATTGT TAAAGTTGCA AAATGTGTTA TTTTTGGTAA GACCCTATGG | 600 |
| ATATATAAAG ACAGGTTATG TGAAACTTGG AAAACCATCA AGTTTTAAGC AAAACCCTCT | 660 |
| TAAGAACTTA AATTGAGCTT CTTTTGGGGC ATTTTTCTAG TGAGAA | 706 |

(2) INFORMATION FOR SEQ ID NO:5:

(i) SEQUENCE CHARACTERISTICS:
        (A) LENGTH: 368 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

| | |
|---|---|
| AGCTTATCTA AACAAAGTTT TAAATTCATT TCTTAAACGT CCATTACAAT GTAATATAAC | 60 |
| TTAGTCGTCT CAATTAAACC ATTAATGTGA AATATAAATC AAAAAAAGCC AAAGGGCGGT | 120 |

| | |
|---|---|
| GGGACGGCGC CAATCATTTG TCCTAGTCCA CTCAAATAAG GCCCATGGTC GGCAAAACCA | 180 |
| AACACAAAAT GTGTTATTTT TAATTTTTTC CTCTTTTATT GTTAAAGTTG CAAAATGTGT | 240 |
| TATTTTTGGT AAGACCCTAT GGATATATAA AGACAGGTTA TGTGAAACTT GGAAAACCAT | 300 |
| CAAGTTTTAA GCAAAACCCT CTTAAGAACT TAAATTGAGC TTCTTTTGGG GCATTTTTCT | 360 |
| AGTGAGAA | 368 |

(2) INFORMATION FOR SEQ ID NO:6:

(i) SEQUENCE CHARACTERISTICS:
        (A) LENGTH: 3426 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: promoter
        (B) LOCATION: 1..1877

(ix) FEATURE:
        (A) NAME/KEY: exon
        (B) LOCATION: 1954..2079

(ix) FEATURE:
        (A) NAME/KEY: intron
        (B) LOCATION: 2080..2375

(ix) FEATURE:
        (A) NAME/KEY: exon
        (B) LOCATION: 2376..2627

(ix) FEATURE:
        (A) NAME/KEY: intron
        (B) LOCATION: 2628..2912

(ix) FEATURE:
        (A) NAME/KEY: exon
        (B) LOCATION: 2913..3284

(ix) FEATURE:
        (A) NAME/KEY: 5'UTR
        (B) LOCATION: 1878..1953

(ix) FEATURE:
        (A) NAME/KEY: CDS
        (B) LOCATION: join(1954..2079, 2376..2627, 2913..3284)

(xi) SEQUENCE DESCRIPTION: SEQ ID NO:6:

| | |
|---|---|
| GGATCCCCCT CTTTTATAAT AGAGGGTCAT TACTTTATTT ACAATAAAAT AATAAAATAA | 60 |
| AGCATATAGT GGAGGACCCA TGATGACTTG TTTCTTCCTC GATTTTCGCC GAGATTCTCT | 120 |
| CCCATAGTGC GGTTGCAACG GCCCTTGTCT GCGAGCTCGA TACTGGTTCG AGCTCGGCAT | 180 |
| TGGACCGAGC CCTCGACCTT GGTCCGAGCT CGATTCTGAC TTGGGGTCTC GGTATTCGGG | 240 |
| GTGAGTGTTG GTCGGTCTAT GCATCTTCGA TAATCTCCGT TTTGCCTCGT AGTTCGATTT | 300 |
| GGATATGAGC TCGATAATGA TACCGAGCTT GTCATTGATC GGTCTTAGAG CTCGAAGTTC | 360 |
| GACGCCTTTA CTTCGGACCT TGACCGAGCT TGTTATGTAG ATATCCTTTG ATCGAAACAT | 420 |
| TATCGTTTTG ACCAATCCGT ACGACTGACT CAAATCGATT TGACCGCACA CAAGATTATT | 480 |
| TTCGAAAGAC CCTCGACGTC TTGGAGTATA AAATAATTTA GTAAAGAGAG TAATTGTTCG | 540 |
| TTAAAAATCT TGACACCATT CCAAGCATAC CCCTTATTGT ACTTCAATTA ATTATCATTA | 600 |
| TATCAGCATA AACATTATAA TAAGTTTCTT GCGTGTTGGA ACGTCATTTT AGTTATTCTA | 660 |
| AAGAGGAAAT AGTTTCTTTT TTGCTCATGA CATCAGACAT CTGGACTACT ATACTGGAGT | 720 |
| TTACCTTTTC TTCTCCTCTT TTTCTTATTG TTCCTCTAAA AAAAATTATC ACTTTTTAAA | 780 |

-continued

```
TGCATTAGTT AAACTTATCT CAACAACGTT TAAAATTCAT TTCTTGAATG CCCATTACAA      840

TGTAATAGTA TAACTTAATT AGTCGTCTCC ATGAACCATT AATACGTACG GAGTAATATA      900

AAACACCATT GGGGAGTTCA ATTTGCAATA ATTTCTTGCA AAAATGTAAA GTACCTTTTT      960

GTTCTTGCAA AATTTTACAA ATAAAAATTT GCAGCTCTTT TTTTTCTCTC TCTCCAAATA     1020

CTAGCTCAAA ACCCACAAAT ATTTTTGAAT TTATGGCATA CTTTTAGAAT GCGTTTGATG     1080

CAACTATTTT CCTTTAGGAA ATATTCACAA CAATCTAAGA CAATCAAAAA GTAGAAAATA     1140

GTTTGTAAAA AGGGATGTGG AGGACATCTT AATCAAATAT TTTCAGTTTA AAACTTGAAA     1200

ATGAAAAAAC ACCCGAAAGG AAATGATTCG TTCTTTAATA TGTCCTACAC AATGTGAATT     1260

TGAATTAGTT TGGTCATACG GTATATCATA TGATTATAAA TAAAAAAAAT TAGCAAAAGA     1320

ATATAATTTA TTAAATATTT TACACCATAC CAAACACAAC CGCATTATAT ATAATCTTAA     1380

TTATCATTAT CACCAGCATC AACATTATAA TGATTCCCCT ATGCGTTGGA ACGTCATTAT     1440

AGTTATTCTA AACAAGAAAG AAATTTGTTC TTGACATCAG ACATCTAGTA TTATAACTCT     1500

AGTGGAGCTT ACCTTTTCTT TTCCTTCTTT TTTTTCTTCT TAAAAAAATT ATCACTTTTT     1560

AAATCTTGTA TATTAGTTAA GCTTATCTAA ACAAAGTTTT AAATTCATTT CTTAAACGTC     1620

CATTACAATG TAATATAACT TAGTCGTCTC AATTAAACCA TTAATGTGAA ATATAAATCA     1680

AAAAAAGCCA AAGGGCGGTG GGACGGCGCC AATCATTTGT CCTAGTCCAC TCAAATAAGG     1740

CCCATGGTCG GCAAAACCAA ACACAAAATG TGTTATTTTT AATTTTTTCC TCTTTTATTG     1800

TTAAAGTTGC AAAATGTGTT ATTTTTGGTA AGACCCTATG GATATATAAA GACAGGTTAT     1860

GTGAAACTTG GAAAACCATC AAGTTTTAAG CAAAACCCTC TTAAGAACTT AAATTGAGCT     1920

TCTTTTGGGG CATTTTTCTA GTGAGAACTA AAA ATG GTG AGG ATT GCC TTT GGT     1974
                                     Met Val Arg Ile Ala Phe Gly
                                       1               5

AGC ATT GGT GAC TCT TTT AGT GTT GGA TCA TTG AAG GCC TAT GTA GCT     2022
Ser Ile Gly Asp Ser Phe Ser Val Gly Ser Leu Lys Ala Tyr Val Ala
         10              15                  20

GAG TTT ATT GCT ACT CTT CTC TTT GTG TTT GCT GGG GTT GGG TCT GCT     2070
Glu Phe Ile Ala Thr Leu Leu Phe Val Phe Ala Gly Val Gly Ser Ala
 25                  30                  35

ATA GCT TAT AGTAAGTAAC ACTTCTCTAA TTAAACTTGC ATGCTAACAT              2119
Ile Ala Tyr
 40

AAATACTTAA TCTGCTCTAG CACTAAATAG TAAAAAGAGC AATCAGGTGC ACTAAGGTCC     2179

CATTAATTCG TTATGCACAT GCCACGGAGT CTAGAGAAAG ACTAGACTGG CTCTATCATA     2239

TTCAATTTTA CCTTACATTT TACTAGATGC CGTTTTCTCA ATCCATAACC GAAAACAACA     2299

TAACTTTTAC AGTTACACCA AGACTGCCTA ATTAACCTTT TTTTTTTTTT TTTTTGCTTT     2359

GTGGGGTGAT TTTGTA GAT AAA TTG ACA GCA GAT GCA GCT CTT GAT CCA        2408
               Asp Lys Leu Thr Ala Asp Ala Ala Leu Asp Pro
                           45                  50

GCT GGT CTA GTA GCA GTA GCT GTG GCT CAT GCA TTT GCA TTG TTT GTT     2456
Ala Gly Leu Val Ala Val Ala Val Ala His Ala Phe Ala Leu Phe Val
         55                  60                  65

GGG GTT TCC ATA GCA GCC AAT ATT TCA GGT GGC CAT TTG AAT CCA GCT     2504
Gly Val Ser Ile Ala Ala Asn Ile Ser Gly Gly His Leu Asn Pro Ala
 70                  75                  80                  85

GTA ACT TTG GGA TTG GCT GTT GGT GGA AAC ATC ACC ATC TTG ACT GGC     2552
Val Thr Leu Gly Leu Ala Val Gly Gly Asn Ile Thr Ile Leu Thr Gly
         90                  95                 100

TTC TTC TAC TGG ATT GCC CAA TTG CTT GGC TCC ACA GTT GCT TGC CTC     2600
```

```
Phe Phe Tyr Trp Ile Ala Gln Leu Leu Gly Ser Thr Val Ala Cys Leu
            105                 110                 115

CTC CTC AAA TAC GTT ACT AAT GGA TTG GTATGTACTG CTATCATTTT              2647
Leu Leu Lys Tyr Val Thr Asn Gly Leu
            120                 125

CAATCCATAT TATATGTCTT TTTATATTTT TCACAACTTC AATAAAAAAA CAACTTTACC      2707

TAAGACCAGC CTAAGCCGTC GTATAGCCGT CCATCCAACC CTTTAAATTA AAAAGAGCCG      2767

GCATAGTCAT AATATATGTA TATTTCATGT AGAATATTTG TATAATTAGT GTATATTGTA      2827

CGTATATCGA CTAGAAAAAA ATAAATAATG AATATGACTG TTTATTTGTA ATTGGAGTTG      2887

GGCCTCATAT GTTGGTTTTT GGCAG GCT GTT CCA ACC CAT GGA GTT GCT GCT       2939
                            Ala Val Pro Thr His Gly Val Ala Ala
                                            130                 135

GGG CTC AAT GGA TTA CAA GGA GTG GTG ATG GAG ATA ATC ATA ACC TTT       2987
Gly Leu Asn Gly Leu Gln Gly Val Val Met Glu Ile Ile Ile Thr Phe
                140                 145                 150

GCA CTG GTC TAC ACT GTT TAT GCA ACA GCA GCA GAC CCT AAA AAG GGC       3035
Ala Leu Val Tyr Thr Val Tyr Ala Thr Ala Ala Asp Pro Lys Lys Gly
                155                 160                 165

TCA CTT GGA ACC ATT GCA CCC ATT GCA ATT GGG TTC ATT GTT GGG GCC       3083
Ser Leu Gly Thr Ile Ala Pro Ile Ala Ile Gly Phe Ile Val Gly Ala
            170                 175                 180

AAC ATT TTG GCA GCT GGT CCA TTC AGT GGT GGG TCA ATG AAC CCA GCT       3131
Asn Ile Leu Ala Ala Gly Pro Phe Ser Gly Gly Ser Met Asn Pro Ala
185                 190                 195

CGA TCA TTT GGG CCA GCT GTG GTT GCA GGA GAC TTT TCT CAA AAC TGG       3179
Arg Ser Phe Gly Pro Ala Val Val Ala Gly Asp Phe Ser Gln Asn Trp
200                 205                 210                 215

ATC TAT TGG GCC GGC CCA CTC ATT GGT GGA GGA TTA GCT GGG TTT ATT       3227
Ile Tyr Trp Ala Gly Pro Leu Ile Gly Gly Gly Leu Ala Gly Phe Ile
                220                 225                 230

TAT GGA GAT GTC TTT ATT GGA TGC CAC ACC CCA CTT CCA ACC TCA GAA       3275
Tyr Gly Asp Val Phe Ile Gly Cys His Thr Pro Leu Pro Thr Ser Glu
                235                 240                 245

GAC TAT GCT TAAAACTTAA AAGAAGACAA GTCTGTCTTC AATGTTTCTT               3324
Asp Tyr Ala
        250

TGTGTGTTTT CAAATGCAAT GTTGATTTTT AATTTAAGCT TTGTATATTA TGCTATGCAA     3384

CAAGTTTGTT TCCAATGAAA TATCATGTTT TGGTTTCTTT TG                         3426

(2) INFORMATION FOR SEQ ID NO:7:

(i) SEQUENCE CHARACTERISTICS:
        (A) LENGTH: 250 amino acids
        (B) TYPE: amino acid
        (D) TOPOLOGY: linear (ii) MOLECULE TYPE: protein (xi) SEQUENCE DESCRIPTION: SEQ ID NO:7:

Met Val Arg Ile Ala Phe Gly Ser Ile Gly Asp Ser Phe Ser Val Gly
 1               5                  10                  15

Ser Leu Lys Ala Tyr Val Ala Glu Phe Ile Ala Thr Leu Leu Phe Val
                20                  25                  30

Phe Ala Gly Val Gly Ser Ala Ile Ala Tyr Asp Lys Leu Thr Ala Asp
            35                  40                  45
```

-continued

```
Ala Ala Leu Asp Pro Ala Gly Leu Val Ala Val Ala Val Ala His Ala
     50                  55                  60

Phe Ala Leu Phe Val Gly Val Ser Ile Ala Ala Asn Ile Ser Gly Gly
 65                  70                  75                  80

His Leu Asn Pro Ala Val Thr Leu Gly Leu Ala Val Gly Gly Asn Ile
                 85                  90                  95

Thr Ile Leu Thr Gly Phe Phe Tyr Trp Ile Ala Gln Leu Leu Gly Ser
            100                 105                 110

Thr Val Ala Cys Leu Leu Leu Lys Tyr Val Thr Asn Gly Leu Ala Val
            115                 120                 125

Pro Thr His Gly Val Ala Ala Gly Leu Asn Gly Leu Gln Gly Val Val
        130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Val Ala
        195                 200                 205

Gly Asp Phe Ser Gln Asn Trp Ile Tyr Trp Ala Gly Pro Leu Ile Gly
    210                 215                 220

Gly Gly Leu Ala Gly Phe Ile Tyr Gly Asp Val Phe Ile Gly Cys His
225                 230                 235                 240

Thr Pro Leu Pro Thr Ser Glu Asp Tyr Ala
                245                 250
```